United States Patent [19]

Hatanaka et al.

[11] Patent Number: 4,667,095

[45] Date of Patent: May 19, 1987

[54] APPARATUS FOR MEASURING THE EXTENT OF DEFORMATION OF A MATERIAL

[75] Inventors: Masayoshi Hatanaka; Tadayuki Uekita, both of Iwaki, Japan

[73] Assignee: Kureha Chemical Industry Company, Ltd., Tokyo, Japan

[21] Appl. No.: 734,030

[22] Filed: May 14, 1985

[30] Foreign Application Priority Data

May 19, 1984 [JP] Japan ................. 59-101411

[51] Int. Cl.$^4$ ............ G01J 3/50; G01L 1/24
[52] U.S. Cl. ................. 250/226; 73/800; 356/32
[58] Field of Search ........... 250/226, 231 R, 231 P; 73/762, 763, 800; 356/32-35

[56] References Cited

U.S. PATENT DOCUMENTS

| | | | |
|---|---|---|---|
| 3,715,915 | 2/1973 | Williams | 356/32 |
| 3,735,143 | 5/1973 | Langford | 250/226 |
| 4,015,465 | 4/1977 | Scott | 356/32 |

Primary Examiner—Edward P. Westin
Attorney, Agent, or Firm—Koda and Androlia

[57] ABSTRACT

A material testing apparatus including holders for material to be tested, a driving unit actuating the holders to plastically deform the material and a measuring unit for measuring the extent of color changes in deformed material. The measuring unit, which is an essential part of the apparatus, includes a light source, a light beam receiving unit and a display device. Light beams emitted from a light source are reflected on the plastically deformed material in the form of a testpiece, and thus reflected light beams are introduced into the light beam receiving unit in which the intensity of the received light beam is detected. Then, the light beams are converted into an electrical value, and digitally displayed on the display device. The driving unit may include a mechanism for changing the rate of deformation of the material. The material is usually subjected to plastic deformation by a stepping motor which changes the rate of deformation of the material. The driving unit may further include a plurality of speed reduction gears which can be replaced as required so as to change the rate of deformation of the material over a wide range. The driving unit also includes a mechanism for bending and stretching the testpieces.

6 Claims, 19 Drawing Figures

APPARATUS FOR MEASURING THE EXTENT OF DEFORMATION OF A MATERIAL

BACKGROUND OF THE INVENTION

1. Field of the Invention

The present invention relates to a material testing apparatus and more particularly to a material testing apparatus of the type including testpiece holders, a driving unit for actuating the holders to plastically deform testpieces made of plastics or the like material and a measuring unit for measuring the extent of color changing of the deformed testpieces (the extent of whitening in the case of testpieces made of plastics) by using an optical system.

2. Prior Art

As is well known, there takes places color changing in the deformed area on a certain material which is subjected to plastic deformation under the effect of bending or stretching force. This color changing is attributable to changing of the structure in the deformed area.

In the case of plastics the plastically deformed area becomes whitened. It is confirmed that an occurrence of the phenomenon of stress whitening is mainly attributable to craze appearing in the form of a stripe extending along a kind of molecule arrangement line, microcrack and deterioration of improving agent added to plastics (for instance, butadien based rubber adapted to be added to the matrix to improve impact strength of the latter). In practice, the phenomenon of stress whitening occurs while the above-noted factors are superimposed one above another.

The phenomenon of stress whitening of plastic material is one of the important items which has been elaborately researched as characteristics of the material. A generally known thing is that there is a tendency that the phenomenon of whitening appears more highly with material having better impact strength during plastic deforming and on the contrary impact strength inherent to the material is reduced when the occurrence of the phenomenon of whitening is intentionally inhibited. Thus, research and development work has been conducted to produce a material having a reduced occurrence of the phenomenon of whitening and excellent impact strength in consideration of the abovementioned tendency. In spite of the requirement for the material as mentioned above the current state or research and development activities is practically such that they are oriented to produce material having a natural well balanced between the extent of whitening and impact strength.

For this reason there is the necessity for conducting a variety of experiments for examining the extent of whitening when new material, particularly new plastic material, is to be developed. Further, there is a necessity for obtaining objective and quantitative data as experimental data which is usable for developing a new material.

As for the hitherto known experiments for examining the extent of stress whitening are concerned which were reported in technical papers or like, they deal mainly with experiments for plastically deforming material under the effect of stretching force. However, in the case where deformation of conventional plastic products are studied, it is necessary to examine the extent of whitening caused not only due to tensile deformation but also due to bending deformation. In practice, no research and development work is reported probably because of the difficulty of determining operative conditions or the like in the case of bending deformation of plastic material.

When plastic material is tested to plastically deform it under the effect of stretching force, the results or measurements conducted with respect to the extent of whitening are hitherto visually evaluated by the operator's eyes. For this reason the results of experiments are usually reported by way of photographs printed on technical papers or the like. Obviously, photographs have different optical contrast depending on the printing condition, and the kind of printing paper or the like, resulting in a failure of obtaining objective data. As another evaluating method, a five point evaluating method is also employed which is intended to evaluate the extent of whitening by using a 1 to 5 scale. In this method a certain numeral thus obtained represents the extent of whitening of plastic material. However, a drawback of the method is that exact measurement is difficult because an operator's subjectiveness tends to be added to the results of the experiments.

SUMMARY OF THE INVENTION

Thus, the present invention has been made with the foregoing background in mind.

It is an object of the present invention to provide a material testing apparatus which assures that color changing caused due to plastic deformation of plastic material is measured objectively and quantitatively.

It is another object of the present invention to provide a material testing apparatus which assures that a rate of deformation of plastic material is changed to obtain a variety of measurement data in view of the fact that the extent of whitening of plastic material does not change depending on the angle of bending and the length of stretching but changes depending on the rate of bending and stretching.

It is another object of the present invention to provide a material testing apparatus which assures that the bending test and tensile strength test are conducted in a single apparatus.

To accomplish the above objects there is proposed, according to the present invention, a material testing apparatus of the type including holders for holding a material to be tested, a driving unit for actuating the holders to plastically deform the material and a measuring unit for measuring the extent of color changing of the deformed material. The measuring unit for measuring the extent of color changing of the material essentially includes a light source for emitting detection light beams toward a specific area on the material of which color has been changed due to plastic deformation, a light beam receiving unit for receiving reflected light beams coming up from the specific area to detect its intensity and a display device for displaying an intensity of detected light beams after converting the latter into an electric value.

Preferably, the driving unit for plastically deforming the material includes a mechanism for changing the rate of deforming the material.

Usually, the material is plastically deformed by operating a stepping motor which has a function of changing the rate of deforming the material.

Alternatively, the driving unit may include a plurality of speed reduction gears which can be replaced as required so as to change the rate at which the material is deformed.

The driving unit includes a mechanism for bending material for the bending test and a mechanism for stretching the material for the tensile strength test.

Other objects, features and advantages of the present invention will become more clearly apparent from reading the following description which has been prepared in conjunction with the accompanying drawings.

BRIEF DESCRIPTION OF THE DRAWINGS

The accompanying drawings will be briefly described below.

DESCRIPTION OF THE PREFERRED EMBODIMENTS

Now, the present invention will be described in a greater detail hereunder with reference to the accompanying drawings which illustrate preferred embodiments thereof.

Figure 1:
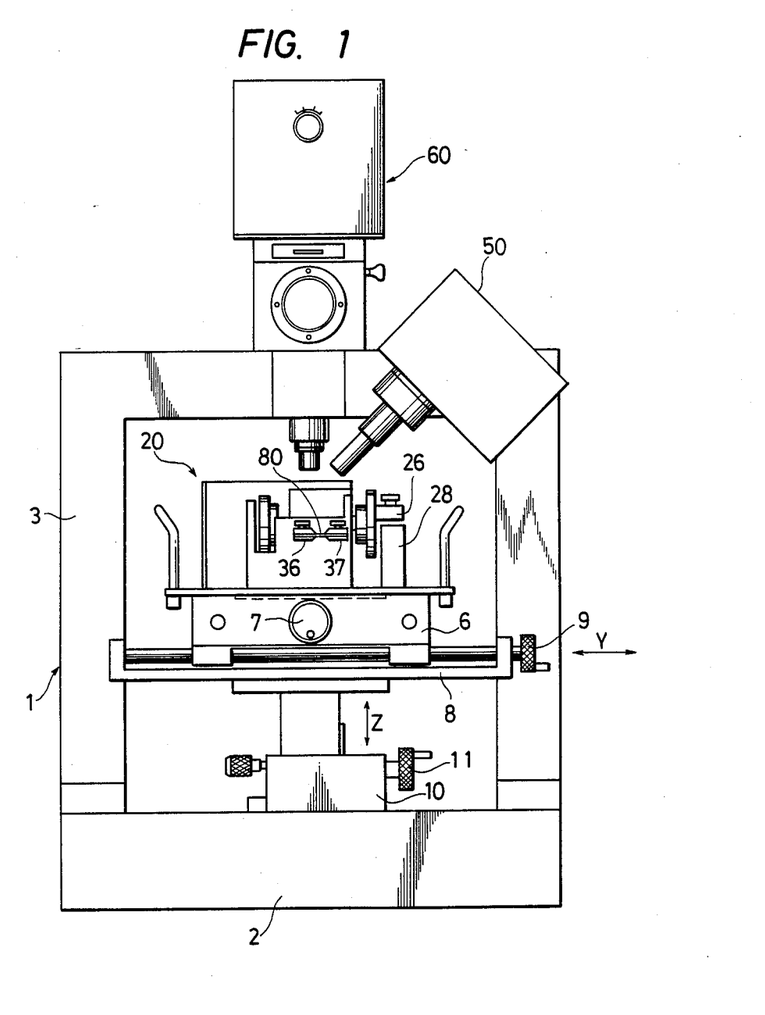
FIG. 1 is a front view of a material testing apparatus according to an embodiment of the invention, illustrating the whole structure thereof.
Figure 2:
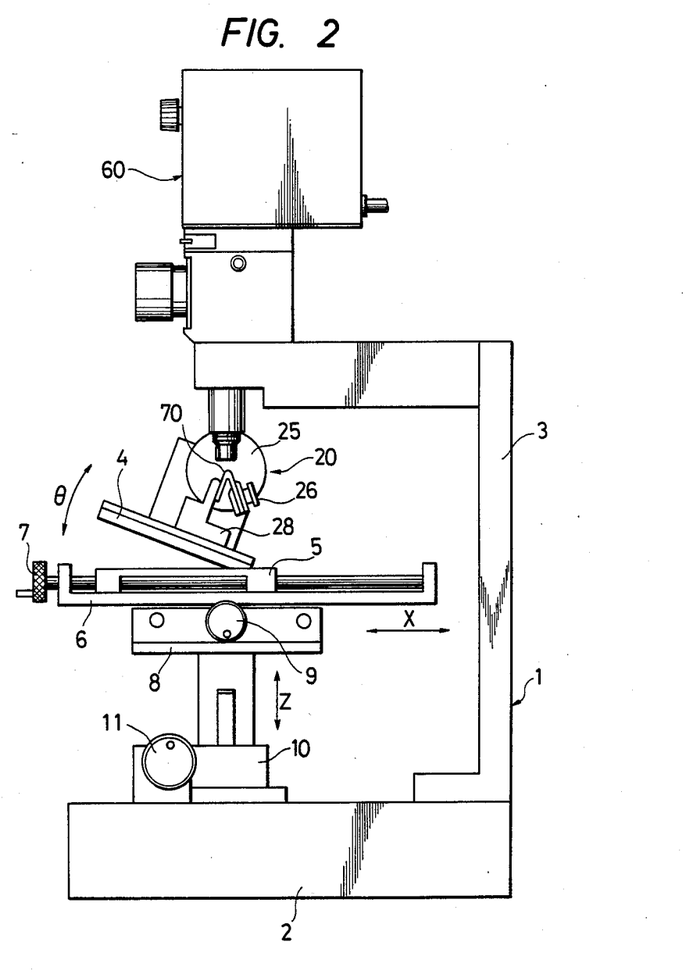
FIG. 2 is a side view of the apparatus of FIG. 1.

FIG. 1 is a front view of a material testing apparatus in accordance with an embodiment of the invention, illustrating the whole structure of the apparatus and FIG. 2 is a side view of the apparatus as seen from the right side in FIG. 1.

In the drawings reference numeral 1 designates a mounting platform, reference numeral 20 denotes a material deforming mechanism, reference 50 denotes a light source and reference numeral 60 denotes a light beam receiving unit.

Specifically, the mounting platform 1 includes a base 2 and a frame 3 upright standing on the base 2. The light source 50 and the light beam receiving unit 60 are supported on the frame 3. The material deforming mechanism 20 is fixedly mounted on an inclinable table 4. As illustrated in FIG. 2, the inclinable table 4 is inclinably supported on a movable table 5 to incline both the directions as identified by arrow marks $\theta$ on the drawing. Arrangement is so made that an inclination angle as measured in either of the directions $\theta$ can be determined by manually rotating a screw shaft or like means. The movable table 5 is movably mounted on an X-coordinate support table 6. When handle 7 is manually rotated, the movable table 5 moves on the X-coordinate support table 5 in either of the X directions. As is apparent from the drawing, the X-coordinate support table 6 is mounted on a Y-coordinate support table 8. When handle 9 is manually rotated, the X-coordinate support table moves on the Y-coordinate support table 8 in either of the Y directions. Further, the Y-coordinate support table 8 is supported on a raising and lowering mechanism 10. When handle 11 is manually rotated, components located above the Y-coordinate support table 8 inclusive of the latter are raised or lowered in either of the Z directions.

Thus, by actuating each of the handles as noted above, a required position of testpieces 70 and 80 held on the material deforming mechanism 20 is properly determined relative to the light source unit 50 as well as the light beam receiving unit 60.

Figure 3:
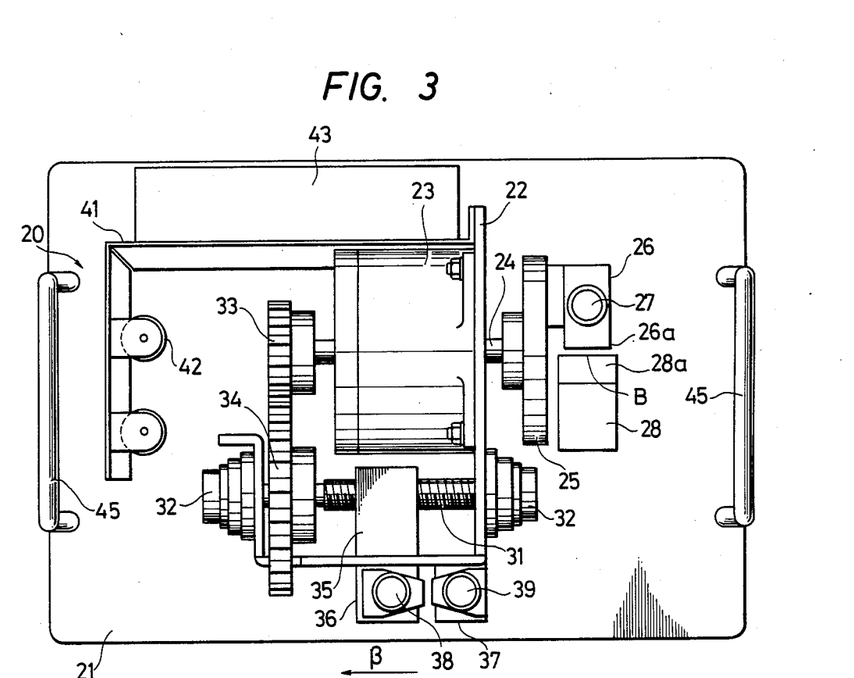
FIG. 3 is a plan view of a material deforming mechanism mounted on the apparatus.
Figure 4:
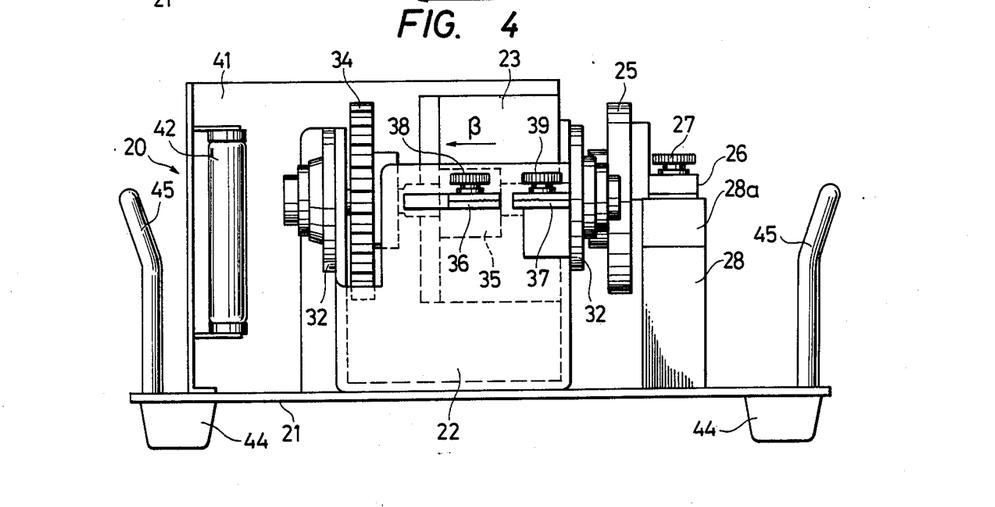
FIG. 4 is a front view of the material deforming mechanism in FIG. 3.
Figure 5:
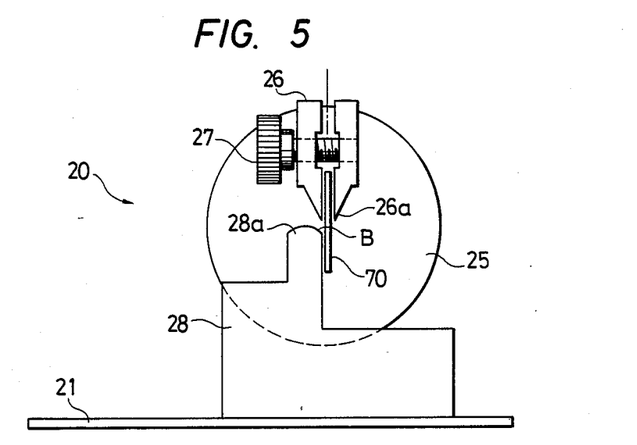
FIG. 5 is a fragmental enlarged side view of the material deforming mechanism in FIG. 4, particularly illustrating a material bending section as seen from the right side of FIG. 4.

FIG. 3 (plan view), FIG. 4 (front view) and FIG. 5 (fragmental side view as seen from the right side in FIGS. 3 and 4, particularly illustrating essential components) illustrate how the material deforming mechanism 20 is constructed.

Figure 6A:
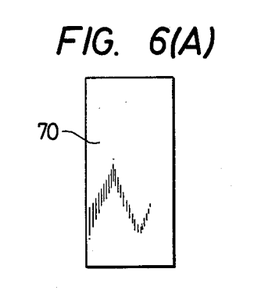
FIG. 6(A) is a front view of a testpiece for bending test.
Figure 6B:
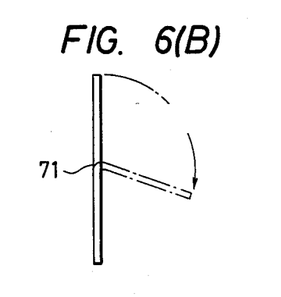
FIG. 6(B) is a side view of the testpiece in FIG. 6(A), illustrating the bent state by phantom lines.
Figure 7:
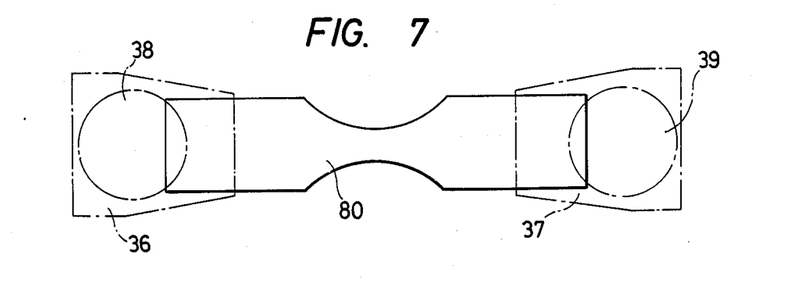
FIG. 7 is a plan view of a testpiece for tensile test.

The material deforming mechanism 20 is used to bend a testpiece 70 (made of plastics) as shown in FIG. 6(A) to the configuration as shown in FIG. 6(B) or to stretch a testpiece 80 (made of plastics) as shown in FIG. 7. A characteristic feature of the material deforming mechanism 20 is that a rate of deforming of each of the teethpieces 70 and 80 can be changed as required.

In the drawings reference numeral 21 designates a base for the material deforming mechanism 20. A holder 22 made of metallic sheet material is fixedly mounted on the base 21 and includes a stepping motor 23 which serves as a driving power source. The stepping motor 23 has a shaft 24 on which righthand end as seen in the drawing, a disc 25 is fixedly secured thereto. The disc 25 is provided with a material holder 26. As is apparent from FIG. 5, the material holder 26 is designed in the form of a chuck adapted to clamp the testpiece 70 between both the holder halves by rotating a knob 27. As illustrated in the drawing, the lowermost end 26a of the holder 26 is located substantially on the center of rotation of the disc 25. Further, a block 28 is fixedly mounted on the base 21. A projection 28a is formed integral with the block 28 and its uppermost end B is located opposite to the lowermost end 26a of the holder 26. After the testpiece 70 is clamped between the holder halves of the holder 26, it is subjected to bending while the uppermost end B of the block 28 serves as an anvil.

As illustrated in FIG. 3, the frame 22 includes an opposing pair of bearings 32 by means of which a screw shaft 31 is rotatably supported. The screw shaft 31 extents in parallel with the shaft 24 of the stepping motor 24. A gear 33 is fixedly mounted on the lefthand end of the shaft 24 of the stepping motor 23 and a gear 34 is fixedly mounted on the lefthand end of the screw shaft 31 as seen in the drawing so that the gear 33 meshes with the gear 34. Further, a slider 35 is threadably engaged to the screw shaft 31. A part of the slider 35 is projected outwardly of the frame 22. The frame 22 is provided with a suitable guide mechanism which is not shown in the drawings so that the slider 35 moves straightly along the foregoing guide mechanism in the direction as identified by arrow mark β (see FIGS. 3 and 4). The slider 35 is formed with a holder 36 at its outermost end. On the other hand, the frame 22 includes a stationary holder 37 which is located opposite to the movable holder 36. The holder 36 is equipped with a knob 38 and the holder 37 is equipped with a knob 39 so that testpiece 80 is held between both the holders 36 and 38 at the outermost ends thereof by rotating the knobs 38 and 39 (see FIG. 7). It should be noted that the position where the testpiece 80 is held by means of the holders 36 and 37 is located substantially in horizontal alignment with the center axis of the shaft 24 of the stepping motor 23, that is, the bent point of the testpiece 70.

A heat radiation plate 41 stands upright on the base 21, and resistors 42 are fixedly mounted on the inside wall of the heat radiating plate 41. Further, a printed circuit board housing section 43 is mounted on the outside wall of the heat radiating plate 41. As illustrated in FIG. 4, a plurality of feet 44 made of rubber are fixedly secured to the bottom of the base 21, and handles 45 are arranged on the base 21.

The material deforming mechanism 20 as constructed in the above-described manner is mounted on the mounting platform 1 by fixedly securing the base 21 onto the inclinable table 4 (see FIG. 2).

Figure 16:
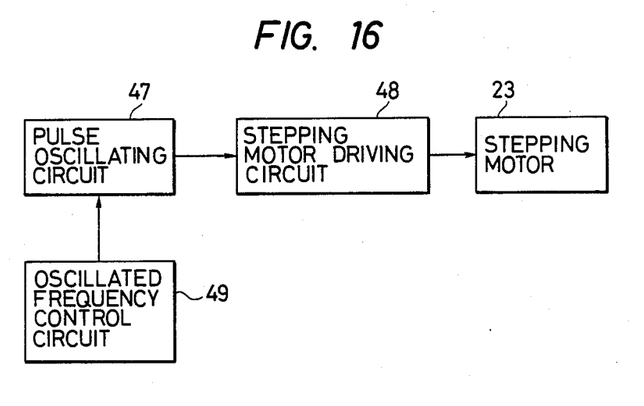
FIG. 16 is a block diagram of an electric circuit for illustrating a driving system for operating the material deforming mechanism.

FIG. 16 shows by way of a block diagram an example of an electric circuit for operating the stepping motor 23. The illustrated circuit is so constructed that a stepping motor driving circuit 48 activates the stepping motor 23 in response to pulses transmitted from the pulse oscillating circuit 47. An oscillating frequency control circuit 49 is constructed with the use of a microcomputer or the like so that rotational speed of the stepping motor 23 can be changed by changing the frequency of the oscillated pulses. Further, it is possible to determine a rotational angle of the stepping motor 23 by controlling the number of oscillated pulses.

Figures 12, 13:
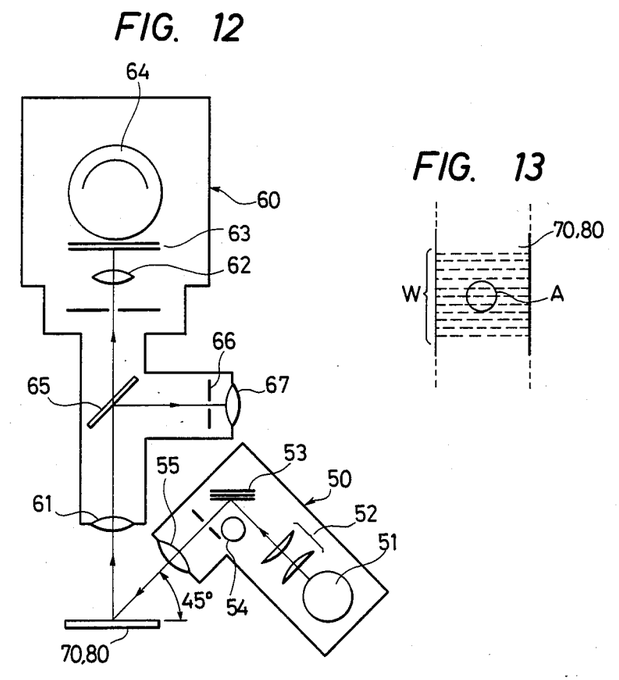
FIG. 12 is a fragmental sectional view of the apparatus, schematically illustrating how a lightening unit and a light beam receiving unit are constructed.
FIG. 13 is a fragmental plan view of a testpiece, particularly illustrating the measuring area on the testpiece.

Next, FIG. 12 schematically illustrates how the light source 50 and the light beam receiving unit 60 are constructed.

Specifically, the light source unit 50 is so arranged that detecting light beams are emitted toward the testpieces 70 to 80 at an inclination angle of 45 degrees relative to the latter. It includes a lamp 51 such as a halogen lamp or the like device. Light beam emitted from the lamp 51 pass through a condenser 52 and then reflected at a mirror 53. Thus the reflected light beams are radiated to the outside via a chopper 54 and a collimeter lens 55.

On the other hand, the light beam receiving unit 60 is oriented at a right angle relative to the testpiece 70 or 80. The light beam receiving element unit 60 has an objective lens 61 at its lowermost end. Further, it has a condenser 62 and a filter 63 which are located in vertical alignment with the objective lens 61 and moreover it has a light beam receiving member 64 such as photomultiplier tube or the like at the uppermost end thereof. It is provided with a semi-transparent mirror 65 at the position located midway of the optical passage and a screen 66, and an eyepiece lens 67 are disposed at the position located rightwardly of the semi-transparent mirror 65 as seen in the drawing.

As schematically illustrated in FIG. 13, detecting light beam emitted from the light source 50 is reflected at the part W on the testpiece 70 or 80 of which color is whitened due to plastic deformation of the testpiece 70 or 80 and its component to be reflected at an angle of 45 degrees is detected by means of the light beam receiving member 64 in the light beam receiving unit 60. In general, the detecting area A is determined to have a diameter in the range of 0.1 to 1.2 m (see FIG. 13).

Figure 15:
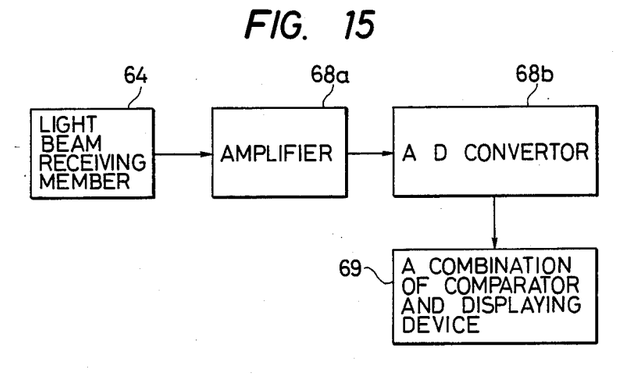
FIG. 15 is a block diagram of an electric circuit by way of which an intensity of output from the light beam receiving member is processed after reflected light beam coming up from the testpiece is detected.

FIGS. 15 shows by way of a block diagram an example of an electric circuit for electrically processing detection output transmitted from the light beam receiving member 64. As an intensity of light beam detected by the light beam receiving member 64 changes, an intensity of electric current outputted from the light beam receiving member 64 is caused to change. Electric current thus outputted from the light beam receiving member 64 is caused to change. Electric current thus outputted from the light beam receiving member 64 is amplified by means of an amplifier 68a and thus amplified electric current is then converted into a digital value in the A/D convertor 68b. Thereafter, it is compared with a reference value by means of a combination of the comparator 69 and display device so that it is displayed numerically or digitally.

Next, operations of the material testing apparatus as constructed in the above-described manner will be described below.

Prior to carrying out tests by operating the material testing apparatus of the invention, a testpiece 70 as shown in FIG. 6(A) or a testpiece 80 as shown in FIG. 7 is previously fabricated. It should be added that the testpiece 70 is used for the bending test and the testpiece 80 is used to the tensile test.

During testing, the testpiece 70 and 80 are subjected to plastic deforming by operating the material deforming mechanism 20. One of the characterizing features of the invention is that the rate of deforming of the testpieces 70 and 80 can be changed as required with the use of the stepping motor 23. It has been confirmed by a number of experiments that the extent of color changing, particularly stress whitening of plastic material caused by deformation of material does not depend on the bending angle of the material but on the bending speed and stretching speed given to the material. Accordingly, it is possible to obtain objective measurement data in in accordance with the testing conditions, provided that the rate of deforming can be changed as required.

Deforming operation of the testpieces 70 and 80 are performed while the material deforming mechanism 20 is fixedly mounted on the inclinable table 4 which is also fixedly mounted on the mounting platform 1. During deforming operation the light source 50 and others are located away from the material deforming mechanism 20 which is displaced by rotating the handles 7, 9 and 11.

As is apparent from FIG. 5, about a half of the length of the testpiece 70 for the bending test is firmly clamped between both the holder halves of the holder 26. While the disc 25 assumes its initial position, the testpiece 70 firmly held by the holder 26 extends in the vertical direction as seen in FIG. 5 and the lower half of the testpiece 70 which is kept free comes in light contact with the side wall of the projection 28a of the block 28. As the disc 25 is rotated by means of the stepping motor 23 in the direction as identified by an arrow mark α in the drawing while the above-mentioned positional state is maintained, the holder 26 is caused to rotate in the same direction whereby the testpiece 70 is bent from the state as shown in FIG. 6(A) to the state as shown in FIG. 6(B). It should be noted that an angular speed of rotation of the disc 25 can be determined when the frequency of pulses is predetermined with the aid of the oscillator frequency control circuit 49. Namely, a rate of bending of the testpiece 70 can be determined as required and therefore data can be obtained every time it is changed. Further, it should be added that an angle of bending of the testpiece 70 can be determined as required by changing the number of pulses.

On the other hand, the testpiece 80 for tensile test is held in such a manner that both ends are firmly clamped between the outside part of the slider 35 and the holder 36 as well as between the projection from the frame 22 and the holder 37 as illustrated in FIG. 7. When the stepping motor 23 starts its operation, rotation of the shaft 24 is transmitted to the screw shaft 31 via the gears 33 and 34 and thereby the slider 35 threadably engaged to the screw shaft 31 is linearly displaced together with the holder 36 in the direction as identified by the arrow mark β in the drawing. Thus, the testpiece 80 is subjected to plastic deformation as it is stretched. Also in this case it is possible to change the rate of plastic deforming oubjected to plastic deformation as it is stretched. Also in this case it is possible to change the rate of plastic deforming of the testpiece 80 and an amount of deformation of the same (an amount of strain) as required by properly changing frequency of pulses or the number of the latter and thereby changing rotational speed and angle of rotation of the stepping motor 23.

After completion of deforming of the tespiece 70 or 80 by operating the material deforming mechanism 20, optical measurement is carried out while the testpiece 70 or 80 is firmly held by means of the holder 36 or 37.

First, a description will be made below as to the bent testpiece 71 (see FIG. 6(B)). Operation is performed such that the optical axis of incident light beam (i) and the optical axis of the reflected light beam (ii) are located in alignment with one another as seen from the side in FIG. 14(B) while they are extended through the apex of the bent testpiece 71 in the vertical direction. At this moment the optical axis of incident light beam (i) is determined to extend toward the ridge line on the bent part of the testpiece 71 at an inclination angle of 45 degrees as seen from the front side in FIG. 14(A), whereas the axis of the reflected light beam (ii) is determined to extend at a right angle relative to the ridge line in the vertical direction.

Figure 14A:
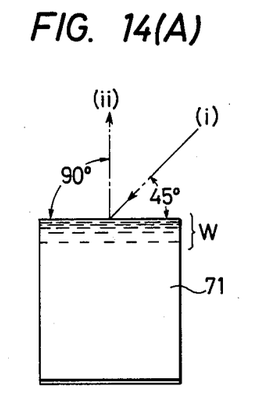
FIG. 14(A) is a front view of the bent tespiece, particularly illustrating how indent light beam is reflected toward the light beam receiving unit at the apex thereof.

On the other hand, with respect to the tensile strength testpiece 80 the axis of the incident line beam (i) is oriented toward the plane thereof at an angle of 45 degrees relative to the latter, whereas the axis of the reflected light beam is oriented at a right angle relative to the plane in the vertical direction.

To determine the position of the testpiece 70 or 80 in the above-described manner, an inclinable table 4 and movable table 5 mounted on the mounting platform 1 are displaced in such a manner described below. Namely, the height of the movable table 5 (as measured in the Z direction) is determined by rotating the handle 11 and its horizontal position as seen in the X direction as well as in the Y direction) is determined by rotating the handles 7 and 9.

Figure 14B:
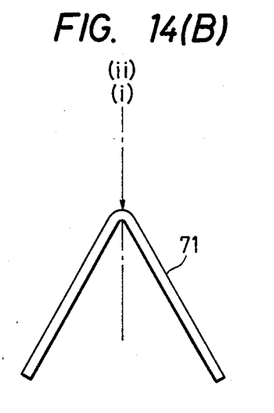
FIG. 14(B) is a side view of the bent testpiece in FIG. 14(A)

In the case of the testpiece 70 for the bending test the inclinable table 4 is inclined in the 0 direction on the movable table 5 so as to allow the axis of indent light beam (ii) to be extended from the apex in the vertical direction, as illustrated in FIG. 2 (see also FIG. 14(B)). On the other hand, in the case of the testpiece 80 for tensile strength test the position of the inclinable table 4 in the X, Y, and Z directions are adjusted while it assumes the horizontal posture whereby detecting light beam is emitted toward the whitened area W.

It should be noted that it is necessary to focus the detecting light beam on the whitened part W and focusing is performed by an operator by observing the screen 66 via the objective lens 67 so as to determine the position of the inclinable table 4 and others while visually confirming the focussed state (see FIG. 12).

When the lamp 51 in the light source 50 is turned on after completion of determination of the required position, thus generated light beam is emitted toward the detecting area A in the whitened part W of the testpiece 70 or 80. An inclined component of reflected light beam having an inclination angle of 45 degrees relative to the passage of incident light beam is then introduced into the light beam receiving unit 60 so that it is detected by means of the light beam receiving member 64. Since the light beam receiving member 64 is adapted to generate electric current corresponding to an intensity of incident light beam, it is amplified in the amplifier 68a and thus amplified electric current is converted into digital value by means of AD convertor 68b. This digital value is then displayed in the form of a numeral. Alternatively, it may be displayed in comparison with a predetermined reference value. An example of reference value is such that a while plate made of magnesium oxide is used a standard plate of which whitened degree is identified as 100 so that a measured value is numerically displayed with reference to the standard value of 100.

Next, FIGS. 8 to 11 illustrate a material bending section in the material bending mechanism in accordance with other embodiments of the invention.

Figure 8:
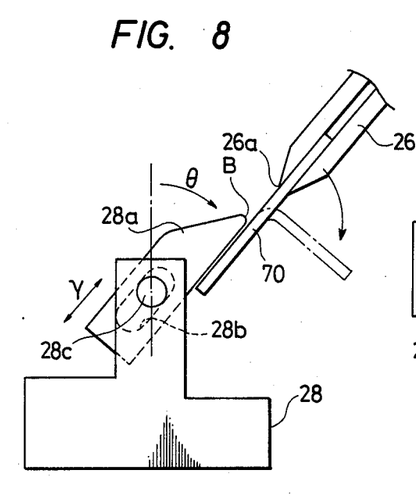
FIG. 8 is a side view of material bending mechanism according to other embodiment of the invention.
Figure 9:
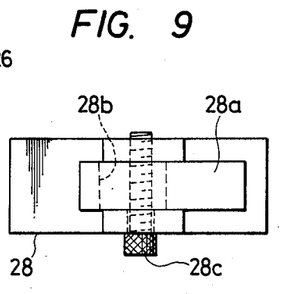
FIG. 9 is a plan view of the material bending mechanism in FIG. 8 as seen from the above.

The material bending section as illustrated in FIGS. 8 and 9 is so constructed that a stationary supporting member 28a is formed with a slot 28b which extends in the longitudinal direction. The stationary supporting member 28a is supported by means of the block 28 on both sides thereof and bolt 28c threadably engaged to the block 28 is inserted through the slot 28b. As is apparent from the drawings, the length of the projection of the stationary supporting member 28a from the block 28 can be adjusted by slidably displacing it relative to the bolt 28c in the slot 28b.

FIGS. 8 and 9 illustrate a most typical structure of the material bending section but the present invention should not be limited only to this. Alternatively, the material bending section may be constructed in the improved manner, as illustrated in FIGS. 10 and 11.

Figure 10:
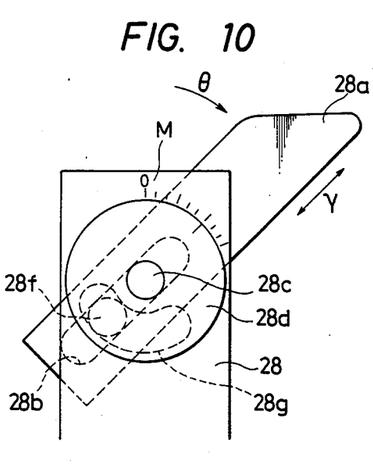
FIG. 10 is a side view of a material bending mechanism according to another embodiment of the invention.
Figure 11:
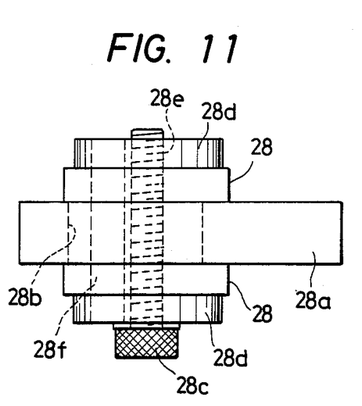
FIG. 11 is a plan view of the material bending mechanism in FIG. 10 as seen from the above.

Specifically, the material bending section as illustrated in FIGS. 10 and 11 has a characterizing feature that the block 28 includes an opposing pair of rotary discs 28d on both sides thereof. The bolts 28c are inserted through the one rotary disc 28d, the block 28 and the slot 28b on the stationary supporting 28a and it is threadably engaged to the female thread hole 28e of the other rotary disc 28d. Further, both the rotary discs 28d are connected to one another by means of an auxiliary shaft 28d which extends therebetween. The auxiliary shaft 28f is also inserted through the slot 28b on the stationary supporting member 28a. Further, the block 28 is formed with an arch-shaped slot 28g through which the auxiliary shaft 28f is free to extend at any position where the stationary supporting member 28a is turned in the inclined state.

Thus, the bolt 28c is loosened from the tightly threaded state, both the rotary discs 28d can be turned together about the bolts 28c while they are connected to one another by means of the auxiliary shaft 28f. As the rotary discs 28d are rotated, the stationary supporting member 28a is caused to turn under the effect of thrusting force given by the auxiliary shaft 28f whereby an inclination angle of $\theta$ can be adjusted as required. Further, the length of projection of the stationary supporting member 28a in either of the directions which is identified by arrow marks $\delta$ in the drawing can be adjusted as required, while displacement of the stationary supporting member 28a along the slot 28b is guided by means of the bolt 28a and the auxiliary bolt 28f. As illustrated in FIG. 10, a number of calibration lines M are impressed on the side wall of the block 28 so as to allow an angle of rotation of the rotary discs 28d to be visually observed during adjusting operation of an inclination angle $\theta$ of the stationary supporting member 28a.

Incidentally, calibration lines may be provided on the side wall of the block 28 in the material bending section as illustrated in FIGS. 8 and 9 in order that an inclination angle $\theta$ of the stationary supporting member 28a is visually observed by an operator. In this case it is preferable that calibration lines are impressed, for instance, on a plate having the semicircular configuration and the thus calibrated plate is fixedly secured to the side wall of the block 28 so that an inclination angle of the stationary supporting member 28a is visually measured by reading a certain calibration line on the plate which is located in alignment with the one edge line of the stationary supporting member 28a.

As will be readily apparent from the above description, there is no necessity for including the inclinable table 4 in either of the directions as identified by arrow marks $\theta$ in FIG. 2, provided that arrangement is made such that an inclination angle $\theta$ of the stationary supporting member 28a can be adjusted in the same manner as in the foregoing embodiments. Further, in this case, no raising and lowering mechanism is required for displacing the inclinable table 14 in the Z direction, because there is no necessity for inclining the inclinable table 4 and moreover instead of the raising and lowering mechanism the stationary supporting member 28a can be projected upwardly or downwardly as required. However, it should be added that another mechanism for raising or lowering both the light source 50 and the light beam receiving unit 60 in the range of several millimeters is required in order to assure that detecting light is correctly focused on the testpiece.

Figure 17:
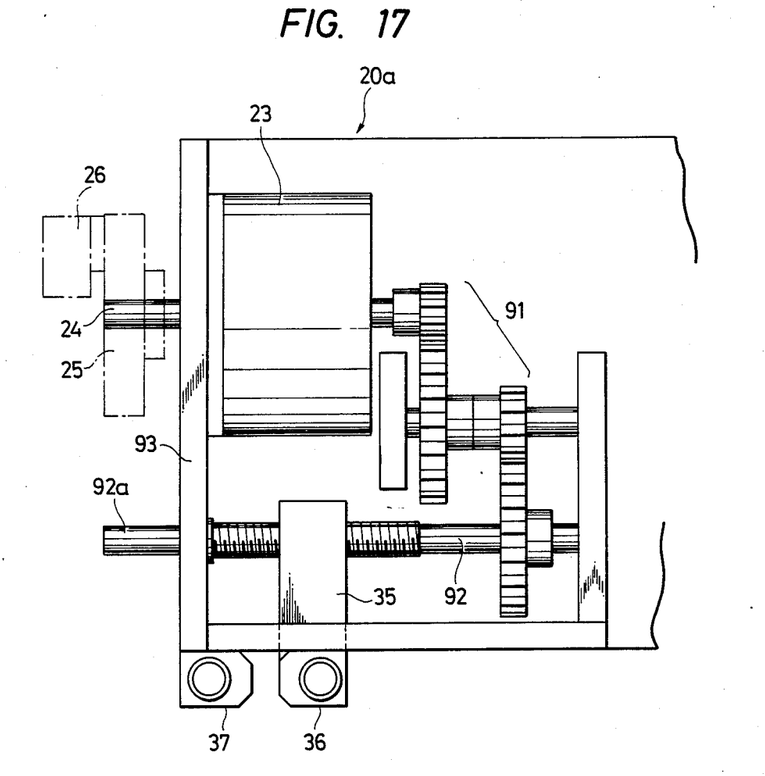
FIG. 17 is a fragmental plan view of the material testing apparatus, particularly illustrating a material deforming mechanism according to further another embodiment of the invention.

Next, FIG. 17 schematically illustrates by way of a plane view a material deforming mechanism 20a in accordance with another embodiment of the invention. In this embodiment a group of gears 91 are interposed between the shaft 24 of the stepping motor 23 and the screw shaft 92 extending in parallel with the shaft 24. By virtue of the arrangement made in that way, the screw shaft 92 can be rotated at a remarkably reduced rotational speed. The slider 35 is threadably engaged to the screw shaft 92 in the same manner as in the case of the first mentioned embodiment.

A characterizing feature of the apparatus according to this embodiment is that the one end 92a of the screw shaft 92 is projected outwardly of a frame 93. Another characterizing feature of the apparatus is that the disc 25 with a holder 26 for holding a testpiece 70 for bending test mounted thereon can be selectively mounted either on the shaft 24 of the stepping motor 23 or on the one end 92a of the screw shaft 92.

The arrangement of the apparatus made in this way makes it possible to widen the effective range of determining rotational speed of the disc 25 adapted to be rotated with a single stepping motor 23. When the group of gears 91 are used for the holder 26, remarkably increased speed reduction ratio can be obtained. Thus, rotational speed of the shaft 24 differs substantially from that of the shaft 24. This means that the range of determining a rate of bending of the testpiece 70 can be widened by selectively mounting the disc 25 onto either one of the shafts. For instance, when rotational speed of the shaft 24 is determined in the range of 45 to 900 degrees/sec., that of the screw shaft 92 is determined in the range of 5 to 100 degrees/sec. Accordingly, a small size stepping motor 23 can be employed for this case. When the structure as illustrated in FIG. 17 is employed for the apparatus, it is necessary that a block 28 (as illustrated in FIG. 5) be provided for each of the shaft 24 and the shaft end 92a or it can be displaced from the axis of the one shaft to that of the other one.

Incidentally, in the above-described embodiments of the invention a photomultiplier tube is employed for the light beam receiving member 64 in the light beam receiving unit 60. However, the present invention should not be limited only to this. Alternatively, a photo-cell or the like optical element can be employed for the apparatus.

The present invention has been described above with respect to the case where plastic material is tested in the material testing apparatus. However, it should not be limited only to this since it is possible to test material other than plastics, for instance, metallic material, ceramics or the like in the apparatus particularly in respect of the extent or color changing caused as a result of deformation.

Now, advantageous features of the present invention will be noted below.

According to the invention the apparatus is constructed such that the light beam receiving member receives reflected light beam coming up from the color changed surface of the material to be tested, the extent of color changing caused due to plastic deformation of the material is detected with reference to the intensity of the reflected light beam, and finally a value of detection is electrically processed so that it is digitally displayed. Thus, the apparatus makes it possible to objectively and quantitatively measure the extent of color changing of a certain material and obtain exact measurement data concerning the material which are very useful for further development of the material.

Further, according to the invention the apparatus includes a driving unit for plastically deforming material to be tested with the use of holders and a control unit for changing operational speed of the holders as required whereby a rate of deforming can be changed as required when the material is plastically deformed with the aid of the holders. In view of the fact that the extent of color changing of a certain material, for instance, the extent of whitening of plastic material varies in dependence on a rate of deformation of the material it is possible to obtain measurement data concerning the extent of color changing corresponding to a required operative condition. As a result, thus obtained data can be objectively processed with reference to definitely determined basic data.

Further, according to the invention the apparatus can deform testpieces with the use of holders and carry out optical measurements while holding them in the thus deformed state. Thus, the measurement can be carried out without necessity for removing testpieces after completion of their deformation while malfunction such as spring-back of testpiece or the like is inhibited for any occurrence. As a result, exact measurement data can be obtained.

While the present invention has been described above with respect to a few prefult, exact measurement data can be obtained.

While the present invention has been described above with respect to a few preferred embodiments thereof, it should of course be understood that it should not be limited only to them but various changes or modifications may be made in any acceptable manner without departure from the spirit and scope of the invention defined by the appended claims.

We claim:

1. A material testing apparatus for measuring the amount of deformation of said material comprising:
   holders for holding said material to be tested;
   a driving unit for actuating said holders to plastically deform the material;
   a measuring unit for measuring the amount of color change of the deformed material, said measuring unit comprising:
   a light source of emitting a light beam toward a specified area on the material of which color has been changed due to plastic deformation;
   a light beam receiving unit for receiving a reflected light beam coming up from said specified area to detect its intensity and for converting said intensity into an electrical value; and
   a display device for displaying an intensity of the detected light beam in response to said electrical value from said receiving unit.

2. A material testing apparatus as defined in claim 1, wherein said driving unit for plastically deforming the material comprises means for changing a rate of deforming the material.

3. A material testing apparatus as defined in claim 2, wherein said means for changing said rate of deforming comprises a stepping motor.

4. A material testing apparatus as defined in claim 2, wherein said means for changing the rate of deforming the material includes a plurality of speed reduction gears which can be replaced as required so as to change said rate of deforming the material within a wide range.

5. A material testing apparatus as defined in claim 1, wherein said driving unit for plastically deforming the material includes means for bending the material for bending test and means for stretching the material for tensile strength test.

6. A material testing apparatus as defined in claim 1, wherein one of said holders is a stationary supporting member of which an inclination angle can be adjusted and the other of said holders is movable by said driving unit to bend said material to be tested.

* * * * *